United States Patent [19]

Fanton et al.

[11] Patent Number: 5,596,411
[45] Date of Patent: Jan. 21, 1997

[54] INTEGRATED SPECTROSCOPIC ELLIPSOMETER

[75] Inventors: Jeffrey T. Fanton, Los Altos; Jon Opsal, Livermore, both of Calif.

[73] Assignee: Therma-Wave, Inc., Fremont, Calif.

[21] Appl. No.: 614,522

[22] Filed: Mar. 18, 1996

Related U.S. Application Data

[63] Continuation of Ser. No. 327,315, Oct. 21, 1994, abandoned.
[51] Int. Cl.$^6$ ............................................. G01J 4/00
[52] U.S. Cl. ........................ 356/369; 356/328; 356/351
[58] Field of Search ........................... 356/364, 365, 356/366, 367, 369, 351, 327, 328; 250/225

[56] References Cited

U.S. PATENT DOCUMENTS

| | | | |
|---|---|---|---|
| 3,316,799 | 5/1967 | Daley et al. | 250/225 |
| 3,397,608 | 8/1968 | Ellis | 356/367 |
| 4,210,401 | 7/1980 | Batten | 356/369 |
| 4,999,014 | 3/1991 | Gold et al. | 356/382 |
| 5,042,951 | 8/1991 | Gold et al. | 356/369 |
| 5,159,412 | 10/1992 | Willenborg et al. | 356/445 |
| 5,166,752 | 11/1992 | Spanier et al. | 356/369 |
| 5,181,080 | 1/1993 | Fanton et al. | 356/381 |
| 5,412,473 | 5/1995 | Rosencwaig et al. | 356/351 |

FOREIGN PATENT DOCUMENTS 2602338  5/1988  France ........................ G01N 21/31

OTHER PUBLICATIONS

International Search Report, mailed Mar. 6, 1996, for International Application No. PCT/US95/12467, with an International filing date of Sep. 27, 1995, 4 pages in length.

Primary Examiner—Richard A. Rosenberger
Attorney, Agent, or Firm—Limbach & Limbach

[57] ABSTRACT

An optical inspection apparatus is disclosed for generating an ellipsometric output signal at a plurality of wavelengths, each signal being representative of an integration of measurements at a plurality of angles of incidence. A polarized, broad band light beam is focused through a lens onto a sample in a manner to create a spread of angles of incidence. The reflected beam is passed through a quarter-wave plate and a polarizer which creates interference effects between the two polarizations states in the beam. The beam is then passed through a filter which transmits two opposed radial quadrants of the beam and blocks light striking the remaining two quadrants. The beam is then focused and angularly dispersed as function of wavelength. Each element of a one dimensional photodetector array generates an output signal associated with a specific wavelength and represents an integration of the phase-sensitive ellipsometric parameter ($\delta$) at a plurality of angles of incidence. A second, independent measurement is taken in order to isolate the signal of interest. In one embodiment, the azimuthal angle of the filter is rotated by ninety degrees. The output signals from the second measurement are subtracted from the corresponding output signals from the first measurement to obtain the phase-sensitive ellipsometric information at a plurality of wavelengths. The ellipsometric information is used to analyze the sample.

22 Claims, 3 Drawing Sheets

INTEGRATED SPECTROSCOPIC ELLIPSOMETER

This is a continuation of application Ser. No. 08/327,315, filed on Oct. 21, 1994, now abandoned.

TECHNICAL FIELD

The subject invention relates to an apparatus for determining the ellipsometric parameters of a sample using a multiple wavelength spectroscopic technique that generates a signal representative of an integration of measurements at multiple angles of incidence.

BACKGROUND OF THE INVENTION

There has been considerable interest in developing high resolution measurement devices for evaluating sample parameters. This need is particularly acute in the semiconductor industry where very thin films, such as oxides, metals or dielectrics, are deposited on semiconductor or metal substrates such as silicon. Non-destructive techniques are particularly needed to evaluate thickness, impurities and index of refraction characteristics of the films to insure high yields during fabrication.

One such inspection device which has been successful in this field is marketed by the assignee herein under the trademark Optiprobe. This device includes an optical measurement system described in U.S. Pat. No. 4,999,014, issued Mar. 12, 1991, to Gold. This system evaluates a sample based on interference effects created when a probe beam interacts with a thin film layer deposited on the surface of a substrate.

In the method described in the Gold patent, a probe beam is focused onto the surface of the sample in a manner to create a spread of angles of incidence. The intensity of rays within the reflected probe beam is measured as a function of the radial position of the ray within the beam using a diode array. The radial position of each ray can be directly related to the angle of incidence that ray with respect to the sample. A processor is used to evaluate the measured intensity of the rays, as a function of angle of incidence, to determine information about the sample.

The concept of obtaining multiple angle of incidence measurements described in U.S. Pat. No. 4,999,014, has more recently been extended to ellipsometry. An ellipsometric system is described in U.S. Pat. No. 5,042,951, issued Aug. 27, 1991, to Gold. The latter patent describes how prior art ellipsometric principles can be enhanced using a simultaneous multiple angle of incidence measurement technique.

In conventional ellipsometric techniques, a probe beam having a known polarization state is directed to interact with the sample. An analyzer is provided to determine the polarization state of the beam after it has interacted with the sample. The change in polarization state of the beam caused by its interaction with the sample is a function of the sample parameters and measurement of this change allows the sample to be analyzed. In a typical measurement scenario, the azimuthal angle of the polarizing or analyzing elements are varied to obtain multiple measurements.

U.S. Pat. No. 5,042,951 describes how ellipsometric information can be obtained at multiple angles of incidence simultaneously. This result is achieved by analyzing the change in polarization state of individual rays within the probe beam as a function of the radial position of the rays. As noted above, the radial position of the rays in the reflected probe beam can be related to the angle of incidence of the rays on the sample. Using an array detector, the ellipsometric parameters are determined simultaneously at multiple angles of incidence.

The measurement approaches described above require analysis of the output of individual elements of a photodetector array. In practice, analysis of these signals can prove challenging since the output of individual detector elements is relatively low.

To overcome this problem, an alternative approach was developed and is described in U.S. Pat. No. 5,181,080 issued Jan. 19, 1993 to Fanton. In the approach described in the latter patent, signal detection is enhanced by using a quadcell photodetector rather than the individual detector elements of an array to measure changes in a probe beam. In operation, a linearly polarized probe beam is tightly focused onto the surface of the sample to create a spread of angles of incidence. The reflected probe beam is passed through a quarter-wave plate to retard the phase of one of the polarization states by ninety degrees. The beam is then passed through a linear polarizer aligned at 45 degrees with respect to the axes of the quarter-wave plate. The polarizer functions to create interference effects between the two polarization states of the beam.

The interference between the two polarization states produces a signal which is proportional to the characteristics (such as thickness) of the film on the sample. This signal, which is a component of the total power of the reflected beam, represents an integration of a plurality of rays at multiple angles of incidence. The relevant signal has a positive sign in two opposed quadrants of the beam and a negative sign in the remaining two quadrants of the beam. Therefore, the relevant signal can be isolated if the entire beam is focused onto the surface of a photodetector which has four detection regions laid out in quadrants. The output signals from two opposed quadrants can be summed and subtracted from the sum of the output signals from the remaining two quadrants. The result of this calculation produces a value which is proportional to certain characteristics of the film, such as film thickness. The approach described in this patent has been implemented in an upgraded version of the device referred to above and is marketed under the designation Optiprobe 2000.

Using a combination of interference measurements and integrated ellipsometry, highly accurate information can be obtained for a variety of films on a variety of substrates. It is well known, however, that the analysis of a sample can be further enhanced if optical measurements are taken at more than one wavelength of light. For example, certain films will exhibit a greater signal response to certain wavelengths. More importantly, obtaining measurements at multiple wavelengths for a given sample can help reduce ambiguities in the analysis. This approach can be particularly useful in situations where the index of refraction of a film is not accurately known or the evaluation is being performed on samples with multiple film layers.

Measurements at multiple wavelengths can be performed relatively easily in a sequential manner. For example, the probe beam can be generated by a white light source. A filtering mechanism is then placed in the path of the white light source and functions to selectively transmit various wavelengths. The filtering mechanism could be defined by a grating, prism or color wheel. Various sequential measurements can then be taken at different wavelengths. The main drawback to this approach is that multiple sequential measurements at different wavelengths can be quite time consuming.

In order to increase the speed of operation, it would be desirable to obtain measurements at multiple wavelengths simultaneously. To achieve this goal, an unfiltered polychromatic light beam is focused onto the sample. After the probe beam has interacted with the sample, some form of dispersing element (prism or grating) can be used to split the probe beam into various wavelength components. This approach is common to many prior art spectrophotometers.

Unfortunately, complications arise when measurements are to be made both at multiple wavelengths and multiple angles of incidence simultaneously. These complications were addressed in copending application Ser. No. 08/093,178, assigned to the same assignee as herein. This application describes an approach wherein a filter having a rectangular slit is used to transmit a narrow band of light lying along a diameter of the probe beam. The filter is positioned in an image plane of the focusing lens to achieve the desired effect. The polychromatic beam passing through this filter is then angularly dispersed as a function of wavelength. Using one or more two dimensional arrays of photodetectors, multiple angle of incidence information at multiple wavelengths could be obtained simultaneously.

The latter application also discloses an embodiment for measuring an ellipsometric signal which is an integration of the multiple angles of incidence. In this embodiment, a filter having a narrow rectangular slit is oriented at 45 degrees with respect to the initial polarization state of the beam. A quarter-wave plate and a polarizing beam splitter are provided to divide the beam into left-hand and right-hand circular polarizations. A pair of dispersing elements are provided to angularly separate the pair of beams as a function of wavelength in a manner to strike a pair of two dimensional array detectors. The output of one row of detector elements of one array is subtracted from the corresponding row of detector elements on the other array to obtain the integration signal of interest at a particular wavelength. Different rows in each array correspond to different wavelengths. It is also possible to subtract the output of a given pixel in one array from the output of the corresponding pixel in the other array to obtain specific multiple angle of incidence information at multiple wavelengths.

The latter approach for obtaining an integrated ellipsometric signal at multiple wavelengths is feasible to implement. However, it is believed that the alternative approach described herein will provide improved results.

SUMMARY OF THE INVENTION

The subject invention provides for an apparatus and method for obtaining an integrated ellipsometric signal at multiple wavelengths. As in the approach described above, a polychromatic light source having a known polarization state is tightly focused through a lens onto the sample to create a spread of angles of incidence. A quarter-wave plate is provided for retarding one of the phases of the beam with respect to the other. A polarizer is provided to create interference effects between the two polarization states.

In accordance with the subject invention, a filter is provided which is located in an image plane of the back focal plane of the focusing lens. The filter is configured to transmit light in two opposed quadrants and block light in the remaining two quadrants. This filter arrangement transmits significantly more light than the narrow slit filter proposed in the above cited application. Since more light is transmitted, the signal strength can be substantially improved.

The consequence of expanding the aperture and increasing the transmission pattern through the filter is that a different detector configuration is necessary to isolate the multiple wavelength data. In the prior approach, the narrow slit in combination with a dispersing element functioned to prevent light of different wavelengths and different angles of incidence from overlapping. Thus, the dispersed light could be directed onto a two dimensional diode array, wherein each row would include full angle of incidence information at a given wavelength. If the prior method of detection were used with a filter having an enlarged aperture as suggested herein, the wavelength and angle of incidence information would become blurred.

To overcome this problem, the detection scheme of the subject invention includes an optical means for focusing the rays of differing angles of incidence while angularly spreading the beam as a function of wavelength. A detector having a single array of detector elements is used to intercept and detect the beam. The light falling on an individual element will be limited to a single wavelength (or narrow band of wavelengths) and represent an integration of rays at varying angles of incidence. It should be noted that by focusing the rays of varying incidence angles on a single element (for each wavelength) greater signal strength can be achieved as compared to the approach discussed above which utilized a two-dimensional array.

Each detector element will generate at signal at a different wavelength that is equivalent to the output signal generated by one of the quadrants of the quad-cell detector described in U.S. Pat. No. 5,181,080 cited above. Thus, the relevant signal of interest will have either a positive or negative sign. In order to isolate the signal of interest, a second, independent measurement must be taken wherein the signal of interest has the opposite sign. The two measured signals can then be subtracted to isolate the signal of interest. This second measurement can be obtained in a variety of ways.

One approach for obtaining the second measurement is to rotate the azimuthal angle of one of the optical elements by ninety degrees. For example, the filter can be rotated so that light in the beam quadrants which had been blocked is now transmitted while the light the was originally transmitted (and measured) is blocked. Another approach would be to rotate the azimuthal angle of the polarizer by ninety degrees while maintaining the rotational angle of the filter in a fixed position.

The second independent measurement can be obtained without rotating any elements if the beam is split and then measured with two sets of independent detector optics. For example, if the beam is split, a pair of filters could be provided each having an aperture configured to transmit light through opposed quadrants. The apertures in the two filters could be disposed at right angles to each other and separate photodetector arrays could be used to obtain the two independent measurements. Other examples for obtaining the two measurements will be discussed below. The approach selected will depend on a determination of the tradeoffs associated with the space and cost requirements associated with the duplication of optical elements versus the complexity of including a rotational mechanism coupled with the need to obtain the two measurements in sequential fashion.

Further objects and advantages of the subject invention will become apparent based on the following detailed description taken in conjunction with the drawings in which:

DETAILED DESCRIPTION OF THE PREFERRED EMBODIMENT

Figure 1:
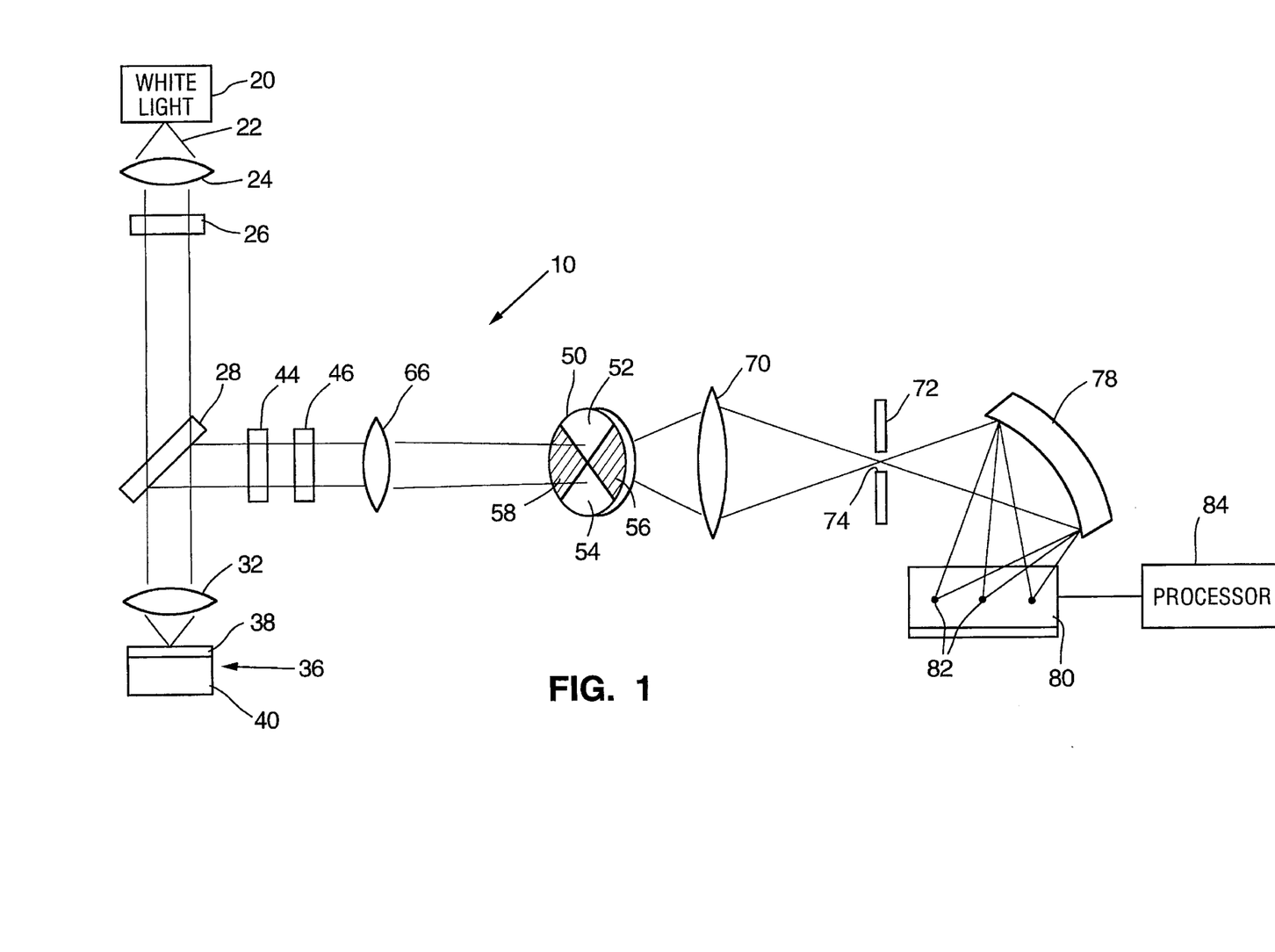
FIG. 1 is a schematic diagram of an apparatus for generating an integrated ellipsometric signal at multiple wavelengths formed in accordance with the subject invention.

FIG. 1 illustrates an apparatus 10 for generating an integrated ellipsometric signal at multiple wavelengths. The apparatus has many similarities to the integrated ellipsometric device described in U.S. Pat. No. 5,181,080. For example, the integrated output signals generated by the subject device 10 are essentially equivalent mathematically to the signals generated by the prior device. The integrated output signal improves measurement accuracy by enhancing the signal to noise ratio over specific angle of incidence measurements. The subject system also permits focusing on the micron scale for high spatial resolution. The primary difference and advantage of the subject invention over the prior device is that the light source is broadband allowing for measurements at multiple wavelengths.

The are a variety of known broad band light sources 20 which could be used to generate the probe beam 22. In an experimental embodiment, a tungsten halogen lamp was utilized. The diverging beam from the lamp is collimated by a lens 24. The beam is then passed through a polarizer 26 to create a known polarization state. In the preferred embodiment, polarizer 26 is a linear polarizer.

The polarized beam 22 is then passed through a beam splitter 28 and directed through a microscope objective lens 32. Preferably, the beam path as it enters the lens is normal to the surface of the sample 36. Sample 36 consists of a thin layer 38 formed on a substrate 40. Lens 32 has a high numerical aperture, on the order of 0.90 NA. The high numerical aperture is intended to tightly focus the probe beam 22 onto the surface of the sample 36 to create rays with a large spread of angles of incidence. This spread can be on the order of 70 degrees. The spot size can be on the order of one micron.

Based on well known ellipsometric principles, upon interaction with the sample, the polarization state of the rays within the beam will change. The reflected beam will therefore have a mixed polarization state as compared with the linear polarization state of the incoming beam. It should be noted that if the substrate is transparent, the probe beam could be analyzed after it has been transmitted through the sample.

Assuming the substrate is substantially opaque, the probe beam will be reflected by the sample, pass back up through the lens 32 and be redirected by splitter 28. The beam is then passed through a means for retarding the phase of one of the polarization states of the beam by ninety degrees. In the preferred embodiment, a quarter-wave plate 44 is used. It should be noted that other phase retarders could be used, but it is believed that a ninety degree phase retardation will maximize the desired signal.

The beam is then passed through a means 46 which functions to cause the two polarization states of the beam to interfere with each other. In the illustrated embodiment, this means is defined by a linear polarizer. In order to maximize the desired signal, the axis of the polarizer should be set at 45 degrees with respect to the fast and slow axes of the quarter-wave plate.

It should be noted that the relative positions of the optical elements shown in FIG. 1 can be varied quite significantly. For example, and as discussed below with reference to the FIG. 5 embodiment, the polarizer can be moved downstream, beyond the filter 50. As another alternative, the quarter-wave plate 44 can be located in the beam path prior to the beam striking the sample. This approach would create a probe beam which was circularly polarized. The latter approach is viewed as less desirable since it is difficult to preserve circular polarization when light is passed through downstream splitters.

In accordance with the subject invention, the probe beam is transmitted to a detector arrangement through a filter or mask 50. Filter 50 is preferably configured to transmit light through two opposed quadrants 52 and 54 while blocking light striking quadrants 56 and 58. The intensity of the beam transmitted by the filter can be viewed as consisting of two fundamental components. The first component is sensitive to the relative optical phase shift between the S and P polarization states (corresponding to the ellipsometric signal δ) while the second component is independent of the optical phase shift. The phase-sensitive component of the signal exists as a positive value in two opposed quadrants and as a negative value in the remaining two quadrants. This result can be appreciated from the following mathematical analysis which is described with reference to linearly polarized light. As noted above, the system can operate with circularly polarized light as well.

In the following analysis, it is assumed that the incident light has the form $E_i(r,\phi)\hat{e}_x$ where r is the radial distance from the center of the beam and $\phi$ is the angle relative to the x-axis. After passing through the objective lens 32, reflecting off of the sample surface, and returning through the lens, the electric field will be spatially dependent and have the form $$E_R(r,\phi)=E_i(r,\phi)\{(R_p \cos^2 \phi + R_s \sin^2 \phi)\hat{e}_x+(R_p-R_s) \sin \phi \cos \phi \hat{e}_y\} \quad (1)$$

where $\hat{e}_x$ and $\hat{e}_y$ are the unit vectors along the x and y axes, $R_p$ is the complex p-wave amplitude reflection coefficient, and $R_s$ is the complex s-wave amplitude reflection coefficient. The radial position within the beam, r, is related to the angle of incidence upon the sample, $\theta$, through the expression $r=d \sin \theta$, where d is the focal length of the objective lens. $R_p$ and $R_s$ are functions of $\theta$ and are independent of $\phi$.

If the beam 22 is passed through the quarter-wave retardation plate 44 oriented such that the x-component is retarded 90° relative to the y-component, and then is passed through the linear polarizer 46 oriented at angle $\alpha$ to the x-axis, the electric field will be of the form $$E_R(r,\phi,\alpha)=E_i[i \cos \alpha(R_p \cos^2 \phi + R_s \sin^2 \phi)\hat{e}_x+\sin \alpha(R_p-R_s) \sin \phi \cos \phi \hat{e}_y] \quad (2)$$

The light intensity is equal to the square of the field magnitude, $I_R=|E_R|^2$. $I_R$ can be expressed in terms of the ellipsometric parameters $\psi$ and $\delta$ through the following relationships:

$$\frac{R_p}{R_s} = \left|\frac{R_p}{R_s}\right| e^{i\delta} \quad (3)$$

and $$\tan\Psi = \left|\frac{R_p}{R_s}\right|. \quad (4)$$

Carrying out the expansion of $|E_R|^2$, we get $$I_R(r,\phi,\alpha) = I_i(r,\phi)|R_s|^2\{[\tan^2\Psi\cos^4\phi + \sin^4\phi]\cos^2\alpha + \quad (5)$$
$$[\tan^2\Psi + 1]\sin^2\phi\cos^2\phi\sin^2\alpha +$$
$$2\tan\Psi\cos\delta\cos^2\phi\sin^2\phi(\cos^2\alpha - \sin^2\alpha) +$$
$$2\tan\Psi\sin\delta\cos\phi\sin\phi\cos\alpha\sin\alpha\}$$

For very thin films, tan $\psi$ is independent of thickness and $\delta$ is linearly proportional to the thickness. Hence, the last term in the above expression is of greatest interest. As noted above, this term is maximized when the analyzer angle, $\alpha$, is 45°.

The total power impinging on each quadrant of the filter 50 is equal to the integral of $I_R$ over the quadrant. If the incident laser beam, $I_i$, is circularly symmetric, the power in each quadrant is given by $$P = \frac{\pi}{16} \int_0^{r_{max}} [(\tan^2\Psi + 1)(2\cos^2\alpha + 1) + 2\tan\Psi\cos\delta(2\cos^2\alpha - 1)] \cdot \quad (6)$$
$$|R_s|^2 I_i(r) r\, dr \pm \cos\alpha\sin\alpha \int_0^{r_{max}} \tan\Psi\sin\delta |R_s|^2 I_i(r) r\, dr$$

The sign of the second integral is positive for two of the opposed quadrants and negative for the remaining quadrants. If the power of the light striking two of the opposed quadrants is summed and subtracted from the sum of the power of the light striking the remaining two quadrants, the result will have a simple form that is linearly proportional to film thickness for very thin films (i.e. less than 100 angstroms):

$$S = 2\cos\alpha\sin\alpha \int_0^{r_{max}} \sin\delta\tan\Psi|R_s|^2 I_i(r) r\, dr \quad (7)$$

$$= \int_0^{r_{max}} \sin\delta\tan\Psi|R_s|^2 I_i(r) r\, dr \quad \text{for } \alpha = 45°. \quad (8)$$

For very thin films or small $\delta$ then $$S = \int_0^{r_{max}} \delta\tan\Psi|R_s|^2 I_i(r) r\, dr \quad (9)$$

The maximum signal of interest S lies along the axis where the maximum interference exists between the S and P polarization states. This interference diminishes along the axes where only S or P polarizations exist. Thus, the azimuthal angle of filter 50 should oriented such that the central region of each quadrant is aligned with the region of maximum interference while the side edges or boundaries of each quadrant should be aligned with the regions of minimum interference.

In order to best isolate the signals of interest, the filter 50 must also be located at an image of the back focal plane (Fourier plane) of lens 32. To achieve this goal, a lens 66 is provided to relay an image of the back focal plane of lens 32 into the plane of the filter 50. Using this approach, the rays passing through lens 32 are mapped onto the filter so the positions of interest are preserved. Each of the quadrants will transmit light which represents a plurality of angles of incidence. The extent of variation in angles of incidence will depend on the numerical aperture of lens 32.

As noted above, the sign of the second integral of equation (6) is positive for two quadrants and negative for the remaining two quadrants. Filter 50 functions to limit the beam in a manner such that the portion of the total transmitted beam power which represents the ellipsometric signal $\delta$ will have only one sign (either positive or negative). The transmitted beam is then passed to a detector structure which will function to integrate the angle of incidence information while segregating the multiple wavelength information. To achieve this goal, the beam transmitted through filter 50 is first focused by a lens 70 through spatial filter. Spatial filter 72 includes a small aperture 74. As discussed below, the diameter of the aperture 74 will govern the wavelength resolution of the detection system.

After passing through filter 72, the light beam is both focused and angularly dispersed as a function of wavelength. In the illustrated embodiment, a curved grating 78 is used to achieve this result. The step of focusing the light functions to combine all of the various angle of incidence information from the transmitted beam in order to create an integrated output. The grating 78 also functions to angularly disperse the light as a function of wavelength in order to isolate the wavelength information. Although a curved grating is shown for simultaneously focusing and dispersing the light, these two functions could be performed by two separate optical elements (i.e. a curved mirror or lens and a separate planar grating or prism).

The focused and angularly dispersed light is directed to a linear photodetector array 80. Array 80 includes a plurality of individual detector elements 82. In an experimental embodiment, the array included 256 elements each spaced apart by about 50 microns. Each element receives and measures the intensity of light over a narrow wavelength region. In the experimental embodiment, using a filter 72 wherein the aperture 74 has a diameter of 150 microns, each element 82 would receive light over a bandwidth of five to six nanometers. In order to increase the power received by the detector elements, the diameter of aperture 74 could be enlarged. However, if the diameter of the aperture is increased, the bandwidth of the light falling on each element would increase, thereby reducing wavelength resolution. In the experimental embodiment using a tungsten halogen light source, the single array detector was able to measure light over a range of more than 300 nm, extending from below 500 nm to above 800 nm.

It should be understood that the detector arrangement shown in FIG. 1, including the spatial filter, grating and photodetector array is similar to the components used in a conventional spectrophotometer. There are therefore a number of other optical lay outs which are available to perform the focusing and dispersing functions of the subject invention. It should also be understood that a conventional spectrophotometer does not include the other elements of FIG. 1, including the optical elements for generating the ellipsometric signal of interest and the filter 50 for isolating that signal.

The output of photodetector 80 is supplied to a processor 84 for evaluation. As noted above, this signal corresponds to the transmitted intensity of the beam. One component of this signal is sensitive to the relative optical phase shift between the S and P polarization states. In order to isolate this component of the signal, a second independent measurement must be taken. This second measurement should be the same as the first measurement with the exception that the phase-sensitive component of the second measurement signal is opposite in sign to the phase-sensitive component of the first measurement. Once the second measurement is obtained, it can be subtracted from the first measurement, allowing the phase-sensitive ellipsometric component of the signal to be isolated from the measurement of the total beam power.

There are a number of methods for obtaining the second independent measurement. One approach would be to rotate the azimuthal angle of the filter by ninety degrees. By this arrangement, the quadrants of the probe beam which had been transmitted will now be blocked while the quadrants of the probe beam which had been blocked will now be transmitted and measured. Due to the geometric principles discussed above, the second measurement of beam power will contain the phase-sensitive component of the signal having a value opposite in sign to the phase-sensitive component of the first measurement. This measurement can be recorded at each element 82 of photodetector array 80. As noted above, each element generates a signal representative of an integration of a plurality of angles of incidence at a different wavelength. By subtracting the signal obtained during the second measurement from the signal obtained during the first measurement, on an element by element basis, the ellipsometric signal of interest can be isolated for a plurality of different wavelengths.

A similar result can be obtained by rotating the azimuthal angle of either the quarter-wave plate 44 or the polarizer 46 by ninety degrees. In each case, basic ellipsometric geometry principles treats any of these rotation variations as theoretical equivalents. In practice, certain real world considerations (such as the fact that optical components are never ideal) impart some distinctions between the approaches. For example, one problem with rotating the polarizer 46 is that the polarization of light passing through various downstream splitters (not shown but typically used for beam steering in a commercial device) will be different and therefore will be transmitted differently. This problem can be avoided by rotating the filter 50. Rotation of the quarter-wave plate has the advantage that, to the first order, small compensation errors present with broadband polarizers could be canceled.

Figure 2:
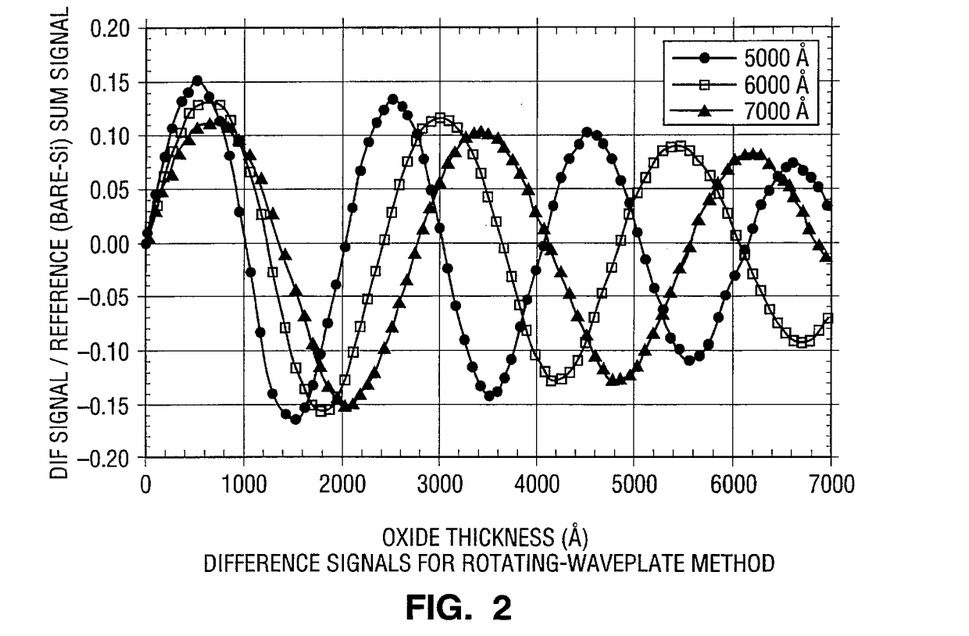
FIG. 2 is a graph plotting data which was obtained when operating the apparatus of FIG. 1 to obtain an integrated ellipsometric signal.

FIG. 2 is a graph of the output signals which were obtained from an experimental version of the device shown in FIG. 1 where the two measurements were obtained by rotating the quarter-wave plate 44. In this experiment, signals from three of the elements 82 of the array were plotted. The elements selected correspond to wavelengths 5000, 6000 and 7000 angstroms.

In the experiment, a sample was provided which was defined by a silicon substrate having an oxide layer which was wedge shaped in cross-section, so that the thickness of the layer varied linearly across the surface. A precision stage was used to move the sample underneath the focused probe beam. The position of the sample was scanned past the probe beam 22 while a series of measurements where taken from the output of the elements 82 and recorded. After a first scan was completed, the azimuthal angle of the quarter-wave plate 44 was rotated by ninety degrees and a second scan, identical to the first scan was performed.

When all of the data had been collected, the processor 84 functioned to subtract the output signal generated by a given element 82 at a given sample position (i.e. at a given layer thickness) during the second scan, from the output signal generated by the same element at the same sample position during the first scan. The result of this subtraction serves to isolate the phase-sensitive component of the signal. This result is then normalized by dividing the signal by the total measured power reflected from bare silicon. The result was then plotted in FIG. 2 at three different wavelengths for a variety of layer thicknesses.

As can be seen, for each wavelength, an integrated, phase-sensitive ellipsometric signal can be derived which varies sinusoidally with layer thickness. By analyzing the signal at additional wavelengths (including intermediate wavelengths not illustrated), much of the inherent ambiguity associated with the sinusoidal response can be removed and layer thickness can be accurately determined.

Figure 3:
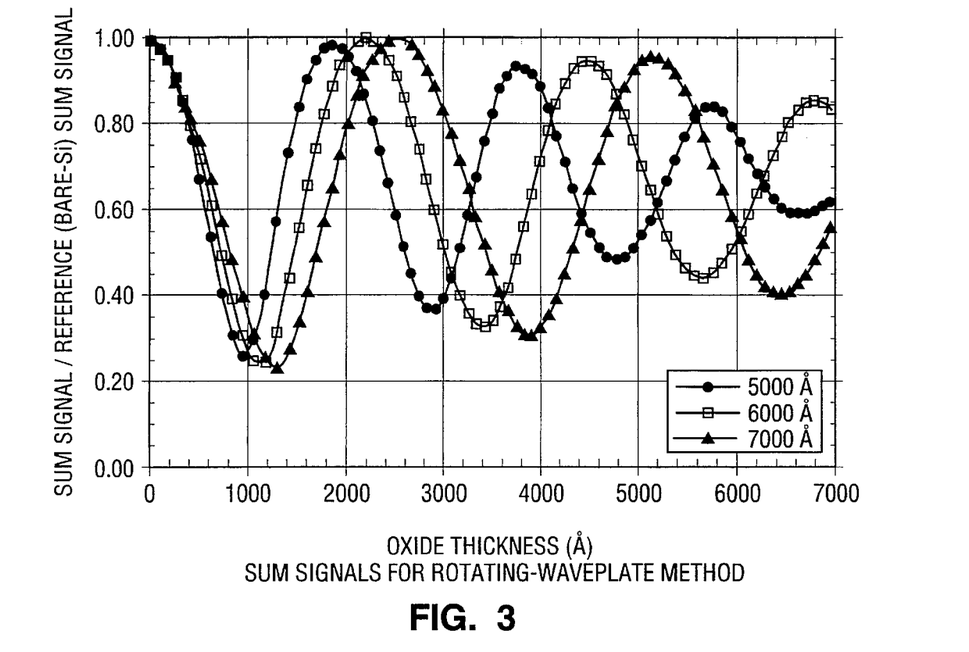
FIG. 3 is a graph plotting data which can be obtained when the system is modified to obtain a conventional spectroscopic signal.

Measurement ambiguities can be further reduced by taking advantage of an easily computed summation signal. The summation or sum signal, which is illustrated in FIG. 3, is the result of adding the output which is obtained from a given element during the two measurement scans. This sum signal is also normalized against a measurement taken on bare silicon. The normalized sum signal is independent of the optical phase shift caused by the sample. The sum signal is essentially equivalent to the output obtained from a more conventional spectrophotometer wherein reflectivity of the sample is measured over a range of wavelengths and is therefore more closely related to the ellipsometric parameter $\psi$. As can be seen in FIG. 3, the summation signal varies sinusoidally with respect to wavelength as well.

One advantage of the sum signal is that it tends to have greater sensitivity in the regions where the difference signal illustrated in FIG. 2 is the least sensitive. Thus, for any given thickness, analysis of the sum and difference signals at multiple wavelengths can be used to produce highly accurate results when analyzing samples. It is also believed that the a broad range of samples and conditions can best be analyzed if the results from the measurement approach described herein is combined with the results from the other optical measurement systems described in the background section of the application.

Having described the basic principals of the operation of the subject device, the remainder of the application will be devoted to a discussion of various approaches for obtaining the two, independent measurements necessary to isolate the ellipsometric signal of interest.

In the embodiment illustrated in FIG. 1, the second measurement was obtained by rotating the azimuthal angle of one of the elements by ninety degrees between scans. This same effect can achieved if the filter 50 was fabricated using a four cell liquid-crystal device wherein each cell could be independently switched from transmissive to opaque. To obtain the first measurement, LCD quadrants 52 and 54 could be made transmissive while LCD quadrants 56 and 58 would be darkened. This pattern would be reversed for the second measurement in a manner equivalent to rotating the filter by ninety degrees.

As can appreciated, in the approaches discussed above, the two independent measurements are taken sequentially and therefore might be viewed as time consuming. However, it should be noted that during each of the two measurements, the output from the full array of elements 82 is recorded, such that information at 256 wavelengths is obtained simultaneously. Thus, even though it is necessary to take two sequential measurements, the data obtained covers a wide range of wavelengths and can be recorded in a time period far shorter than if sequential measurements were necessary for each wavelength.

While the added time to take two measurements is relatively minimal, it might be desirable to design a system which does not require a rotational mechanism. Two alternatives which can be used to obtain both independent measurements simultaneously, without moving parts, are illustrated in FIGS. 4 and 5 and discussed below.

Figure 4:
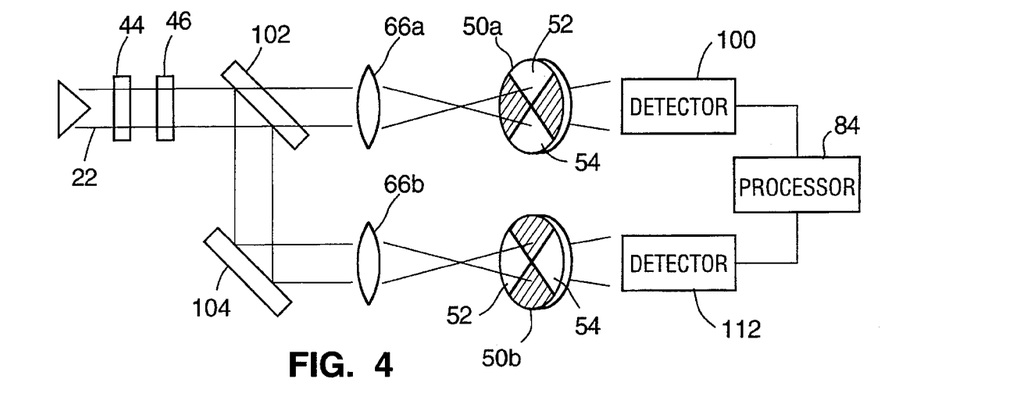
FIG. 4 is a schematic diagram of a second embodiment of the apparatus of the subject invention.
Figure 5:
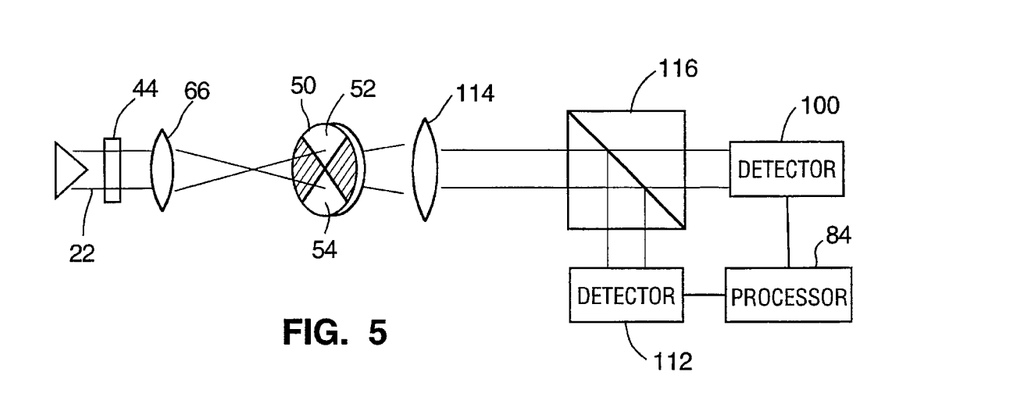
FIG. 5 is a schematic diagram of a third embodiment of the apparatus of the subject invention.

FIG. 4 illustrates a relatively simple variation from the embodiment shown in FIG. 1. As in the first embodiment, the reflected probe beam 22 is passed through a retarder 44 and a polarizer 46. The probe beam is then divided into two equal halves by a splitter 102. One half of the beam is then imaged onto a filter 50a by relay lens 66a. The other half of the beam is imaged onto filter 50b by relay lens 66b (after being turned by mirror 104). Filters 50a and 50b have the same configuration as filter 50 in FIG. 1. In this embodiment, the transmissive quadrants 52 and 54 of filter 50a are oriented orthogonally with respect to the transmissive quadrants 52 and 54 of filter 50b. By this arrangement, the phase-sensitive signal of interest transmitted by filter 50a will be opposite in sign to phase-sensitive signal of interest transmitted by filter 50b.

The beam halves are then directed to detector arrangements 110 and 112 for focusing and angularly dispersing the beam, and measuring the output signal as a function of wavelength. The detectors 110, 112 can consist of the elements shown in FIG. 1 (lens 70, filter 72, grating 78 and photodetector 80) or any other suitable system. The output of the detectors is supplied to the processor 84 for evaluation. Processor 84 will function to generate a difference signal wherein the output signals from detector 110 is subtracted from the corresponding output signals from detector 112 to determine the integrated ellipsometric parameters. The processor can also derive a sum signal as discussed above. Both of these signals can be normalized.

In the approach shown in FIG. 4, the probe beam is split after passing through the polarizer 46. Other variations are possible. For example, a beam splitter could be inserted between the quarter-wave plate 44 and the polarizer 46. In this case, two polarizers would be necessary. The remainder of the lay out could be the same as in FIG. 4. Alternatively, the axis of the polarizer in one leg of the system could be oriented perpendicular to the axis of the polarizer in the other leg. In this case, the two filters 50a and 50b would both be oriented with the same azimuthal angle since the phase-sensitive component in a given beam quadrant in one leg of the beam path will be opposite in sign to the phase-sensitive component in the same quadrant in the other leg of the beam path.

Another approach for obtaining both independent measurements is illustrated in FIG. 5. In this embodiment, the reflected probe beam 22 is passed through a quarter-wave plate 44. An image of the beam at lens 32 is then imaged onto filter 50 which transmits light through two quadrants 52 and 54. The diverging light is then collimated by lens 114 and directed into polarizing beam splitter 116. Polarizing beam splitter functions to divide the beam into two halves, one right-hand circularly polarized and the other left-hand circularly polarized. Each beam half is directed to a detector arrangement 110, 112 which functions to focus the beam while angularly deviating the beam as a function of wavelength. Each detector generates an output signal at a plurality of wavelengths, each of which represents an integration of a plurality of angles of incidence.

As in the case of the embodiment of FIG. 4, the processor 84 functions to isolate the phase-sensitive component by subtracting the output signals generated by one detector from the corresponding output signals generated by the other detector. This calculation is performed at a plurality of wavelengths. A sum signal can also be computed. With this data, the sample can be analyzed.

Figure 6:
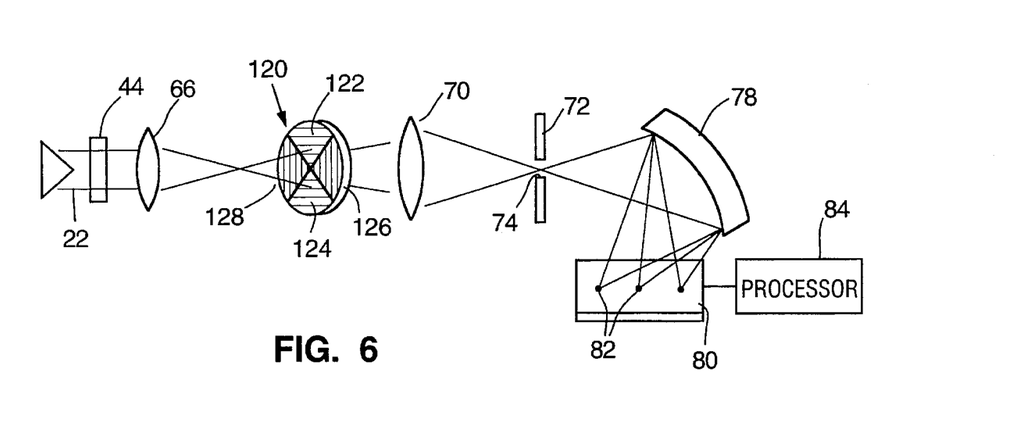
FIG. 6 is a schematic diagram of a third embodiment of the apparatus of the subject invention.

FIG. 6 illustrates still another approach for obtaining two independent measurements. In this embodiment, the reflected probe beam 22 is passed through a quarter-wave plate 44. A lens 66 relays an image of the beam at lens 32 to a filter 120. Filter 120 has four quadrants 122–128. Each quadrant includes a transmissive polarizing element which functions to create interference between the two polarization states of the beam. The axis of polarization in quadrants 122 and 124 is orthogonal to the axis of polarization in quadrants 126 and 128.

This arrangement effectively combines the operative features of the polarizer 46 and filter 50 of FIG. 1. In the FIG. 1 embodiment, the sign of the phase-sensitive component of the signal in quadrants 52 and 54 was opposite to the sign of the phase-sensitive component of the signal in quadrants 56 and 58. In the embodiment of FIG. 6, since the axes of the polarizers in the two opposed quadrant pairs are perpendicular to each other, the sign of the phase-sensitive component of the signal passing through all of the quadrants will be the same.

After the beam passes through filter 120, it is focused by lens 70 through filter 72 and onto grating 78. Grating 78 functions to focus and angularly disperse the light as a function of wavelength. The elements 82 of photodetector array 80 generate an output signal which represents an integration at various angles of incidence as a function of wavelength. The phase-sensitive component of interest in this signal will have a single sign (positive or negative). One approach for obtaining the second independent measurement is to rotate the azimuthal angle of the quarter-wave plate 44 by ninety degrees. This will change the sign of the phase-sensitive component of the signal reaching the detector. As in the first embodiment, the output from a given element 82 generated during the second measurement can be subtracted from the output generated by the same element during the first measurement to isolate the ellipsometric signal of interest. One advantage to the embodiment of FIG. 6 is that all of the light is transmitted by the filter, as compared to only half of the light which is transmitted by the filter of FIG. 1. By transmitting all of the light, the signal strength can be enhanced.

The apparatus of the embodiments in FIGS. 1 and 6 could be used in an alternate method wherein measurements at multiple azimuthal angles are taken, rather than at just two specific azimuthal angles. In this alternate approach, the azimuthal angle of one of the polarizing elements can be rotated and measurements taken at multiple azimuthal angles. If enough measurements are taken at multiple angular positions ($\theta$), a Fourier analysis could be performed on the data.

A Fourier analysis will produce three terms. A DC term will be generated which corresponds to the sum signal discussed above. Another term (sin $2\theta$) will provide the difference signal (sin $\delta$). A third term (cos $2\theta$) will give a result that depends upon cos $\delta$. These terms can be mathematically analyzed in accordance with known ellipsometric principles to extract the relevant parameters $\psi$ and $\delta$.

The embodiments shown in the figures discussed above illustrate that there are a number of optical configurations which can be used to obtain integrated ellipsometric signals at multiple wavelengths. Each of the approaches includes a broad band light source for generating a probe beam having a variety of wavelengths. This probe beam must be polarized and focused onto the sample to create a spread of angles of incidence. A means is provided for retarding the phase of one of the polarization states with respect to the other. A means is also provided to create interference between the two polarization states. An optical filter functions to transmit light in two opposed beam quadrants. A means is provided for focusing the light and angularly dispersing the light as a function of wavelength. A one dimensional photodetector array is used to generate an output signal at each wavelength which is an integration of a plurality of angles of incidence.

A second independent measurement must be taken to isolate the phase-sensitive component of the signal. These two measurements may be taken sequentially. The second measurement can be obtained by rotating the azimuthal angle of any of a number of the optical components. In the alternative, the beam could be divided and both independent measurements can be taken simultaneously. In any event, the phase-sensitive signal of interest is derived by subtracting one measurement from the other at each wavelength. The two measurements can also be added to obtain an output related to the ellipsometric parameter $\psi$. The results of this calculation can be used to evaluate the sample.

While the subject invention has been described with reference to the preferred embodiments, various changes and modifications could be made therein, by one skilled in the art, without varying from the scope and spirit of the subject invention as defined by the appended claims.

We claim:

1. An apparatus for evaluating a sample comprising:

a source for generating a beam of polychromatic light;

means for polarizing the light beam;

lens means for focusing the light beam onto the surface of the sample in a manner so that various rays within the beam create a spread of angles of incidence;

means for retarding the phase of one polarization state of the light beam;

means for creating interference effects between the two polarization states of the beam after it has interacted with the sample;

filter means located in an image plane of the lens means for filtering the light beam, said filter means for transmitting at least a portion of the light passing through a first radial quadrant and blocking light from the two radial quadrants disposed orthogonally thereto;

optical means for focusing the transmitted light and angularly dispersing the focused light as a function of wavelength;

means for measuring the intensity of the focused light as a function of position;

means for obtaining a second independent intensity measurement of light having the characteristics of the light which was blocked by said filter means during the first intensity measurement; and processor means for evaluating the sample based on the independent measurements, wherein said measurements represent an integration of rays at various angles of incidence.

2. An apparatus as recited in claim 1 wherein said means for obtaining the second independent measurement includes a means for rotating the azimuthal angle of one of the polarizing means, retarding means, interference creating means and filter means by ninety degrees.

3. An apparatus as recited in claim 1 further including a means for rotating the azimuthal angle of one of the polarizing means, retarding means, interference creating means and filter means and for taking measurements at multiple azimuthal angles.

4. An apparatus as recited in claim 1 wherein said means for obtaining the second measurement includes splitting the light beam after it has interacted with the sample and providing a second filter means and optical means and measuring means oriented to measure light having the characteristic of the light that was blocked by the filter means during the first intensity measurement.

5. An apparatus as recited in claim 1 wherein said means for creating interference effects consists of a polarizer formed integrally with the filter means.

6. An apparatus as recited in claim 5 wherein the first quadrant of said filter as well as the quadrant disposed opposite thereto include a linear polarizer for polarizing light along a first axis and wherein said two orthogonally disposed quadrants of said filter include a linear polarizer for polarizing light along a second axis orthogonal to the first axis.

7. An apparatus as recited in claim 1 wherein said means for polarizing the light beam is a linear polarizer.

8. An apparatus as recited in claim 1 wherein said means for retarding the beam is a quarter-wave plate.

9. An apparatus as recited in claim 1 wherein said means for creating interference effects is a linear polarizer.

10. An apparatus as recited in claim 1 wherein said means for creating interference is defined by a polarizing beam splitter for dividing the beam into two halves with different polarization states and further including a second optical means and detector means for obtaining the second measurement.

11. An apparatus as recited in claim 1 wherein said optical means includes a curved grating.

12. An apparatus as recited in claim 1 wherein measuring means includes a one-dimensional photodetector array.

13. An apparatus as recited in claim 1 wherein said filter means is formed from a liquid crystal device configured such that the transmission of radial quadrants can be selectively controlled.

14. An apparatus for evaluating a sample comprising:

a source for generating a beam of polychromatic light;

means for polarizing the light beam;

lens means for focusing the light beam onto the surface of the sample in a manner so that various rays within the beam create a spread of angles of incidence;

means for retarding the phase of one polarization state of the light beam;

means for creating interference effects between the two polarization states of the beam after it has interacted with the sample;

filter means located in an image plane of the lens means for filtering the light beam, said filter means for transmitting a portion of the light passing through a pair of opposed radial quadrants and blocking light from the remaining pair of radial quadrants disposed orthogonally thereto;

optical means for focusing the transmitted light and angularly dispersing the focused light as a function of wavelength;

means for measuring the intensity of the focused light as a function of position;

means for rotating the azimuthal angle of one of the polarizing means, retarding means, interference creating means and filter means by ninety degrees allowing said measuring means to perform an independent measurement of the intensity of the focused light; and processor means for evaluating the sample based on the independent measurements, wherein said measurements represent an integration of rays at various angles of incidence.

15. An apparatus as recited in claim 14 wherein said means for polarizing the light beam is a linear polarizer.

16. An apparatus as recited in claim 14 wherein said means for retarding the beam is a quarter-wave plate.

17. An apparatus as recited in claim 14 wherein said means for creating interference effects is a linear polarizer.

18. An apparatus as recited in claim 14 wherein said optical means includes a curved grating.

19. An apparatus as recited in claim 14 wherein measuring means includes a one-dimensional photodetector array.

20. An apparatus as recited in claim 14 wherein said filter means is formed from a liquid crystal device configured such that the transmission of radial quadrants can be selectively controlled.

21. An apparatus for evaluating a sample comprising:

a source for generating a beam of polychromatic light;

means for initially polarizing the light beam;

lens means for focusing the light beam onto the surface of the sample in a manner so that various rays within the beam create a spread of angles of incidence;

means for retarding the phase of one polarization state of the light beam;

filter means located in an image plane of the lens means for filtering the light beam, said filter means including a first linear polarizer formed in a pair of opposed radial quadrants and a second linear polarizer formed in the remaining pair of quadrants disposed orthogonally thereto, and wherein the axis of polarization of the first linear polarizer is disposed orthogonally with respect to the axis of polarization of the second linear polarizer;

optical means for focusing the transmitted light and angularly dispersing the focused light as a function of wavelength;

means for measuring the intensity of the focused light as a function of position;

means for rotating the azimuthal angle of one of the polarizing means, retarding means, interference creating means and filter means by ninety degrees allowing said measuring means to perform an independent measurement of the intensity of the focused light; and processor means for evaluating the sample based on the measurements, wherein said measurements represent an integration of rays at various angles of incidence.

22. A method for evaluating a sample comprising:

generating a beam of polychromatic light;

polarizing the light beam;

focusing the light beam through a lens onto the surface of the sample in a manner so that various rays within the beam create a spread of angles of incidence;

retarding the phase of one polarization state of the light beam;

creating interference effects between the two polarization states of the beam after it has interacted with the sample;

filtering the light beam in a manner to transmit a the portion thereof passing through a pair of opposed radial quadrants and blocking light from the remaining pair of radial quadrants disposed orthogonally thereto, said filtering step being performed in an image plane of the lens;

focusing the transmitted light and angularly dispersing the focused light as a function of wavelength;

measuring the intensity of the focused light as a function of position;

obtaining a second independent intensity measurement of light having the characteristics of the light which was blocked during the first intensity measurement; and processor means for evaluating the sample based on the independent measurements, wherein said measurements represent an integration of rays at various angles of incidence.

* * * * *